(12) United States Patent
Razzano et al.

(10) Patent No.: US 7,194,064 B2
(45) Date of Patent: Mar. 20, 2007

(54) IMAGE CAPTURE DEVICE AND METHODS

(75) Inventors: Michael R. Razzano, Marietta, GA (US); Ronald C. Webb, Red Lion, PA (US); Barry R. Margraf, Chalfont, PA (US)

(73) Assignee: Interactive Diagnostic Imaging, Inc., Marietta, GA (US)

( * ) Notice: Subject to any disclaimer, the term of this patent is extended or adjusted under 35 U.S.C. 154(b) by 0 days.

(21) Appl. No.: 11/063,959

(22) Filed: Feb. 23, 2005

(65) Prior Publication Data

US 2006/0188064 A1 Aug. 24, 2006

(51) Int. Cl.
*H05G 1/64* (2006.01)

(52) U.S. Cl. .................. 378/98.8; 378/38; 378/168; 378/193

(58) Field of Classification Search ............ 378/38–40, 378/119, 121, 145, 147, 193, 197, 204, 98, 378/98.8, 168
See application file for complete search history.

(56) References Cited

U.S. PATENT DOCUMENTS

| | | | |
|---|---|---|---|
| 1,923,669 A | 8/1933 | Harrison | 378/170 |
| 2,090,933 A | 8/1937 | Bolin | 378/170 |
| 2,392,109 A | 1/1946 | Vlock | 378/170 |
| 3,092,721 A | 6/1963 | Medwedeff et al. | 378/170 |
| 3,304,422 A | 2/1967 | Medwedeff | 378/170 |
| 3,304,423 A | 2/1967 | Medwedeff | 378/170 |
| 3,473,026 A | 10/1969 | Updegrave | 378/170 |
| 4,507,798 A | 3/1985 | Welander | 378/170 |
| 4,554,676 A | 11/1985 | Maldonado et al. | 378/170 |
| 4,815,117 A | 3/1989 | Waldo | 378/168 |
| 4,949,370 A | 8/1990 | Tanaka | 378/170 |
| 5,090,047 A | 2/1992 | Angotti et al. | 378/170 |
| 5,289,522 A | 2/1994 | Kanbar et al. | 378/170 |

(Continued)

FOREIGN PATENT DOCUMENTS

KR 2002008810 1/2002

(Continued)

OTHER PUBLICATIONS

"Focused Diagnostics: Sirona Intraoral X-Ray System," http://www.sirona.com/ecomaXL/index.php?site=SIRONA_COM_intrxray_heliodent, accessed Sep. 17, 2004.

(Continued)

*Primary Examiner*—Courtney Thomas
(74) *Attorney, Agent, or Firm*—Woodard, Emhardt, Moriarty, McNett & Henry LLP

(57) ABSTRACT

A novel image capture device, system and method are disclosed for use in capturing dental images. A novel collimator tube includes one or more devices integrated within its wall, such as a radio frequency transmitter, a camera, a frame grabber, or a transilluminator light. The integrated devices are used instead of or in addition to an x-ray generator, which is coupled to the collimator tube. The camera is used to capture digital images. The camera is either a camera port for plugging in an external camera, such as an intra-oral camera, or is wholly contained within the collimator tube. The radio frequency transmitter transmits digital data to a remote computer. The frame grabber captures digital data for display on a display device. The transilluminator light can illuminate an area for digital capture. A novel receptor holder includes a docking port for docking a sensor that is used for digital x-ray capture.

57 Claims, 9 Drawing Sheets

U.S. PATENT DOCUMENTS

| | | | |
|---|---|---|---|
| 5,327,477 A | 7/1994 | Levy | 378/168 |
| 5,652,779 A | 7/1997 | Levy et al. | 378/170 |
| 5,866,914 A * | 2/1999 | Jones | 250/505.1 |
| 6,033,111 A | 3/2000 | Winters et al. | 378/170 |
| 6,575,624 B2 | 6/2003 | Noegel et al. | 378/198 |
| 6,628,751 B2 * | 9/2003 | Eikenberg | 378/98.12 |
| 2002/0076002 A1 | 6/2002 | Eppinger et al. | 378/170 |
| 2005/0002494 A1 | 1/2005 | Diederich | 378/170 |
| 2005/0013412 A1 | 1/2005 | Calderwood et al. | 378/170 |
| 2005/0047550 A1 | 3/2005 | Yao et al. | 378/170 |
| 2005/0053199 A1* | 3/2005 | Miles | 378/197 |
| 2005/0254625 A1* | 11/2005 | Schick et al. | 378/98 |

FOREIGN PATENT DOCUMENTS

KR        2002009527        2/2002

OTHER PUBLICATIONS

"X-Ray Positioning System," http://www.dentalproducts.net/xml/product/display_product.asp?file=15557&tab=search, p. 1, accessed Apr. 23, 2004.

"A Method to Calculate Angular Disparities Between Object and Receptor in Paralleling Technique," Dentomaxillofacial Radiology (2002) 31, Nature Publishing Grp., pp. 32-38.

* cited by examiner

IMAGE CAPTURE DEVICE AND METHODS

BACKGROUND

In today's medical profession, there are various ways to capture images of patients, such as images captured for diagnostic purposes. For example, a medical professional such as a dentist can use a traditional x-ray device to capture a film-based x-ray image of the patient's mouth. Medical professionals can also capture an x-ray image in a digital fashion using a digital x-ray device that has a computer workstation and a sensor. Digital cameras are also used by medical professionals to capture still and video images for later storage on a computer in the patient record. Each of the devices and systems typically require separate systems and pieces of equipment. There is a need for improved devices, systems and methods for capturing images.

SUMMARY

One form of the present invention is a unique image capture device. Other forms include unique systems and methods to capture images. Yet another form includes a unique collimator tube. Another form includes a unique receptor holder.

Another form includes a unique image capture device, system and method for use in capturing dental images. A unique collimator tube includes one or more devices integrated within its wall, such as a radio frequency transmitter, a camera, a frame grabber, or a transilluminator light. The integrated devices are used instead of or in addition to an x-ray generator, which is coupled to the collimator tube. The camera is used to capture digital images. The camera is either a camera port for plugging in an external camera, such as an intra-oral camera, or is wholly contained within the collimator tube. The radio frequency transmitter transmits digital data to a computer. The frame grabber captures digital data for display on a display device. The transilluminator light can illuminate an area for visual inspection and/or digital capture. A unique receptor holder includes a docking port for docking a sensor that is used for digital x-ray image capture.

Yet other forms, embodiments, objects, advantages, benefits, features, and aspects of the present invention will become apparent from the detailed description and drawings contained herein.

DETAILED DESCRIPTION

Figure 1:
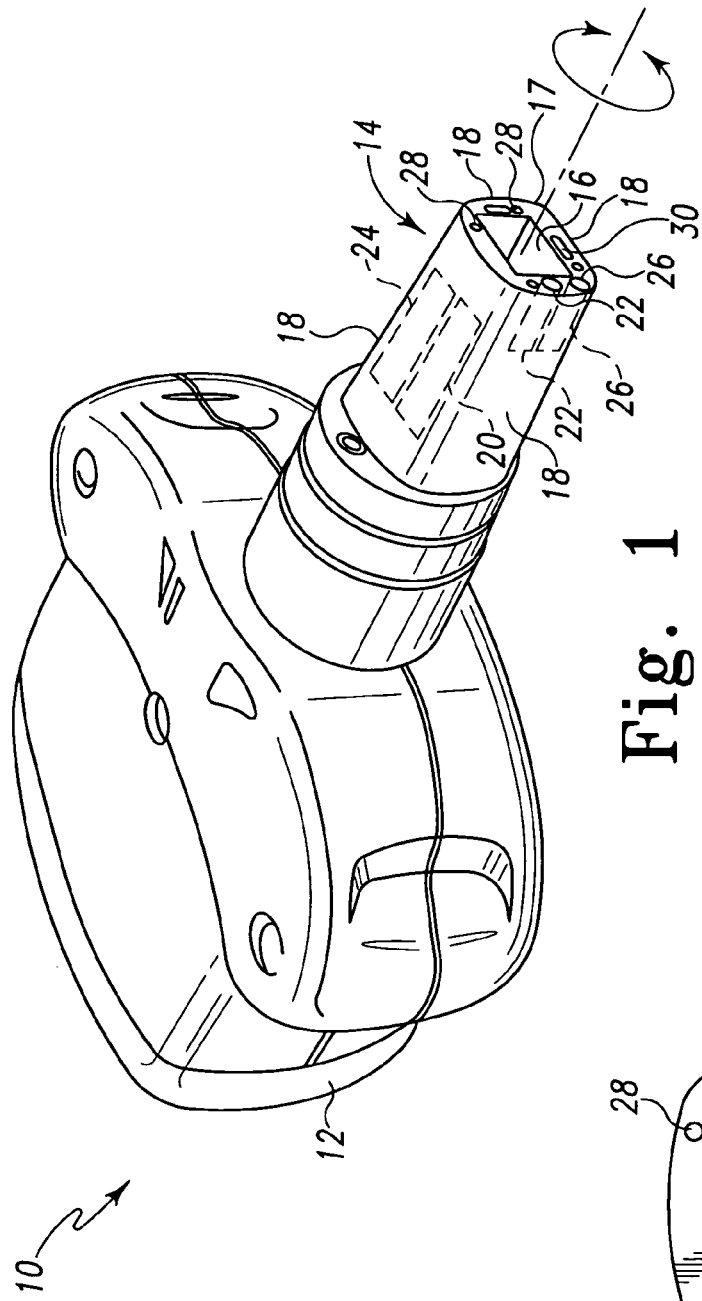
FIG. 1 is a perspective view of an image capture device with an x-ray collimator tube of one embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present invention relates to an image capture device, system and method for use in capturing medical images. A collimator tube includes one or more integrated devices, such as a radio frequency transmitter, a camera, a frame grabber, or a transilluminator light. In one embodiment, the integrated devices are integrated within one or more walls of the collimator tube. The integrated devices are used instead of or in addition to an x-ray generator, which is coupled to the collimator tube. The camera is used to capture digital images. The camera is either a camera port for plugging in an external camera, such as an intra-oral camera, or is wholly contained within the collimator tube. The radio frequency transmitter transmits digital data to a computer. The frame grabber captures digital data for display on a display device. The transilluminator light can illuminate an area for visual inspection and/or digital capture. A receptor holder includes a docking port for docking a sensor that is used for digital x-ray image capture.

Referring to FIG. 1, one embodiment of the image capture device of the present invention is illustrated and indicated generally at 10. Image capture device 10 is operable to capture x-ray images. The image capture device 10 illustrated in FIG. 1 includes x-ray generator 12 and collimator tube 14. Collimator tube 14 serves as the means for focusing x-rays produced by the x-ray generator 12. Alternatively or additionally, collimator tube 14 also decreases scatter radiation and/or decreases absorbed radiation, thereby lowering the patient's x-ray dose. In one embodiment, collimator tube 14 has a square shape in cross section. Collimator tube 14 can also be rectangular, star, cross or round in cross section shape, as a few additional non-limiting examples.

In one embodiment, collimator tube 14 is fixed to x-ray generator 12 and cannot be removed. In another embodiment, collimator tube 14 is detachable from x-ray generator 12, such as by removing one or more screws or other securing means. Alternatively or additionally, collimator tube 14 can be a collimator tube of one shape that replaces a previously attached collimator tube of a different shape. One non-limiting example includes detaching a round-shaped collimator tube and replacing it with a rectangular-shaped collimator tube.

Collimator tube 14 has a tunnel 16 for emitting x-rays and a receptacle 30 for receiving a sliding bar of a receptor holder. Collimator tube 14 has an end 17 that serves one or more purposes. One purpose of end 17 is for coupling a receptor holder to collimator tube 14. Collimator tube 14 has one or more devices integrated within walls 18. In one embodiment, at least one integrated device is visible at least in part from end 17. In one embodiment, collimator tube 14 has a radio frequency transmitter 20, a camera/port 22, a frame grabber 24, and/or a transilluminator light 26 integrated within one or more of walls 18.

Each of these integrated devices will now be described in further detail with reference to FIGS. 1 and 2. Radio frequency (RF) transmitter 20 is operative to send data captured with image capture device 10 to an RF receiver external to image capture device 10. For example, the RF receiver may be coupled to a remotely-located computer for the display and/or processing of images captured by the device 10. As one non-limiting example, RF transmitter 20 can transmit data captured with camera 22 to an external computer. In this way, images captured by image capture device 10 may be downloaded to a computer system for current and/or later use without the need to physically couple the image capture device 10 to the computer. This greatly improves the maneuverability and usefulness of the image capture device 10.

Figure 3:
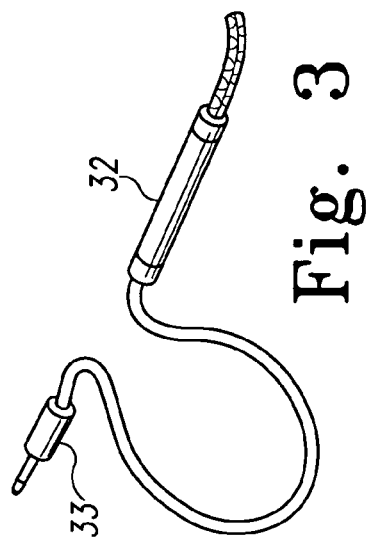
FIG. 3 is perspective view of an intra-oral camera that can be connected to the collimator tube in one embodiment of the current invention.

In one embodiment, the camera 22 is built into the collimator tube 14 and is able to capture images visible from a lens or aperture formed into the end of the collimator tube 14. In another embodiment, camera 22 is an electrical port for allowing an external camera device to plug into collimator tube 14 for transmission of data from the external camera device to the collimator tube 14 integrated devices. One non-limiting example of an external camera device includes intra-oral camera 32 as shown in FIG. 3. The intra-oral camera 32 includes an electrical plug 33 that interfaces with the camera 22 port in the collimator tube 14 for transmitting data captured by the camera 32. Cameras 22 and 32 are operative to capture still images and/or video images in various embodiments. Provision of the external intra-oral camera 32 allows for easy access to the inner regions of the patient's mouth.

In one embodiment, frame grabber 24 is operative to capture still and/or video images for display on an external video display device, such as on a television or a computer display, as is known in the art. Frame grabber 24 is integrally formed with collimator tube 14 to receive image information from one of the image devices integrated with image capture device 10, such as camera 22/32 or the x-ray image receptor 44 (see FIG. 4). The output of frame grabber 24 is preferably coupled to the RF transmitter 20 for transmission of the frame data to a receiving computer and/or display device.

Transilluminator light 26 aids the image capture process by allowing for a light to be shined through a tooth, body or organ, as a few non-limiting examples. The light that is transmitted through the tooth can then be captured using the camera 22/32. For use with the camera 22 formed integrally with the collimator tube 14, means must be provided for directing the light from the transilluminator light 26 to the opposite side of the tooth as the camera 22. This may be done by use of an appropriate mirror (not shown), or by making the transilluminator light 26 an external device that plugs into a port in the collimator tube 14, similar to the intra-oral camera 32. Additionally, the transilluminator light 26 may emit light from the collimator tube 14 and the light transmitted through the tooth may be captured using the intra-oral camera 32.

Various other device combinations are also possible, such as fewer or additional devices than described herein, or a combination of those described. Power may be supplied to these devices by using the internal power supply of the image capture device 10, as will be apparent to those skilled in the art after reference to the above description.

In one form of the invention, collimator tube 14 has contact sensor receptacles 28 that are used to mate an image receptor holder (see FIGS. 8–10) to the collimator tube 14. Contact sensor receptacle 28 can be one or more of various types, such as electrical, mechanical, optical, fiber optic, magnetic or of other connection types as would occur to one in the art. As one non-limiting example, contact sensor receptacles can be used to form a purely mechanical connection between the image receptor holder and the collimator tube 14. Alternatively or additionally, contact sensor receptacles 28 can be used to ensure a receptor holder is attached before firing x-ray generator 12. Alternatively or additionally, one or more lights can be illuminated to indicate the status of the connection, such as green to indicate a proper connection with collimator tube 14 has been made and the x-ray generator is ready to fire, and red to indicate the x-ray generator is not ready to fire, to name a few examples. Alternatively or additionally, a light can be illuminated to indicate that a proper connection has been made, and the light is not illuminated when a proper connection is not made. Alternatively or additionally, an audible sound can be emitted to indicate that a proper connection has been made. In one embodiment, contact sensor receptacles 28 are used with receptor holder 50 illustrated in FIGS. 8–10. Alternatively or additionally, collimator tube 14 has a contact end receptacle 30 formed therein and operative to receive a contact end of a receptor holder. In one embodiment, contact end receptacle 30 is used with the receptor holder illustrated in FIG. 11.

Figure 4:
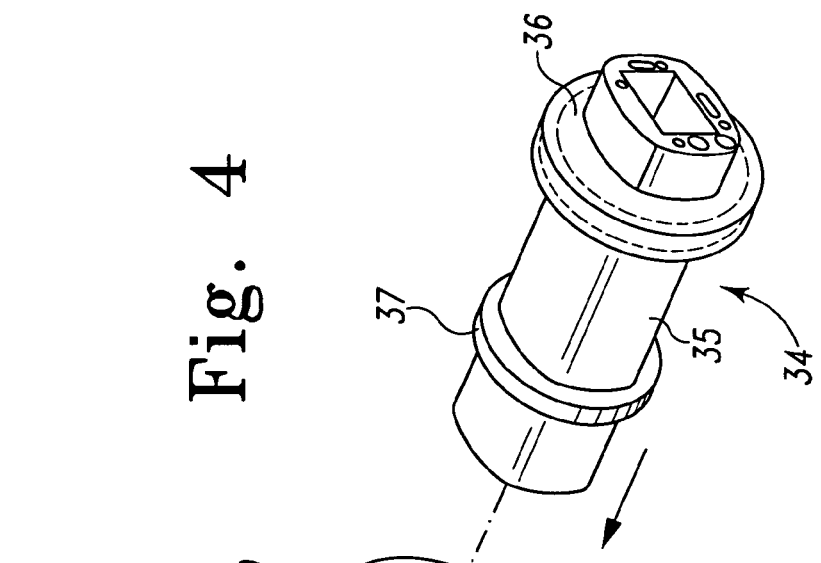
FIG. 4 is a partial perspective view of a collimator tube of one shape being converted to a collimator tube of another shape using a collimator tube adapter in one embodiment of the current invention.

In yet another embodiment, as illustrated in FIG. 4, collimator tube adapter 34 is used to convert collimator tube 38 to a different shape. As one non-limiting example, collimator tube adapter 34 is used to convert collimator tube 38 from a round shape to a rectangular or other shape. Collimator tube adapter 34 includes cone 35, cap 36, and spacer 37. Cap 36 can slide to adjust cone 35 to different depths so cone 35 can fit properly inside collimator tube 38. Various mechanisms can be used to lock cap 36 into a desired location on cone 35, such as using detents or a snap ring, to name a few non-limiting examples. Spacer 37 is used to help secure cone 35 inside collimator tube 38, since cone 35 is a different shape than collimator tube 38. Various types of spacers can be used, such as a washer or an o-ring, to name a few non-limiting examples. Cap 36 is operable to form a seal around end 39 of collimator tube 38.

Although not numbered on FIG. 4 to preserve clarity, in one embodiment, collimator tube adapter 34 has one or more devices integrated within its walls. These devices can be integrated within walls of collimator tube adapter 34 instead of or in addition to devices integrated in collimator tube 38. Collimator tube adapter 34 and collimator tube 38, when used together, can include the same devices and perform the same functions as described herein with respect to collimator tube 14 of image capture device 10 on FIG. 1.

Figure 5:
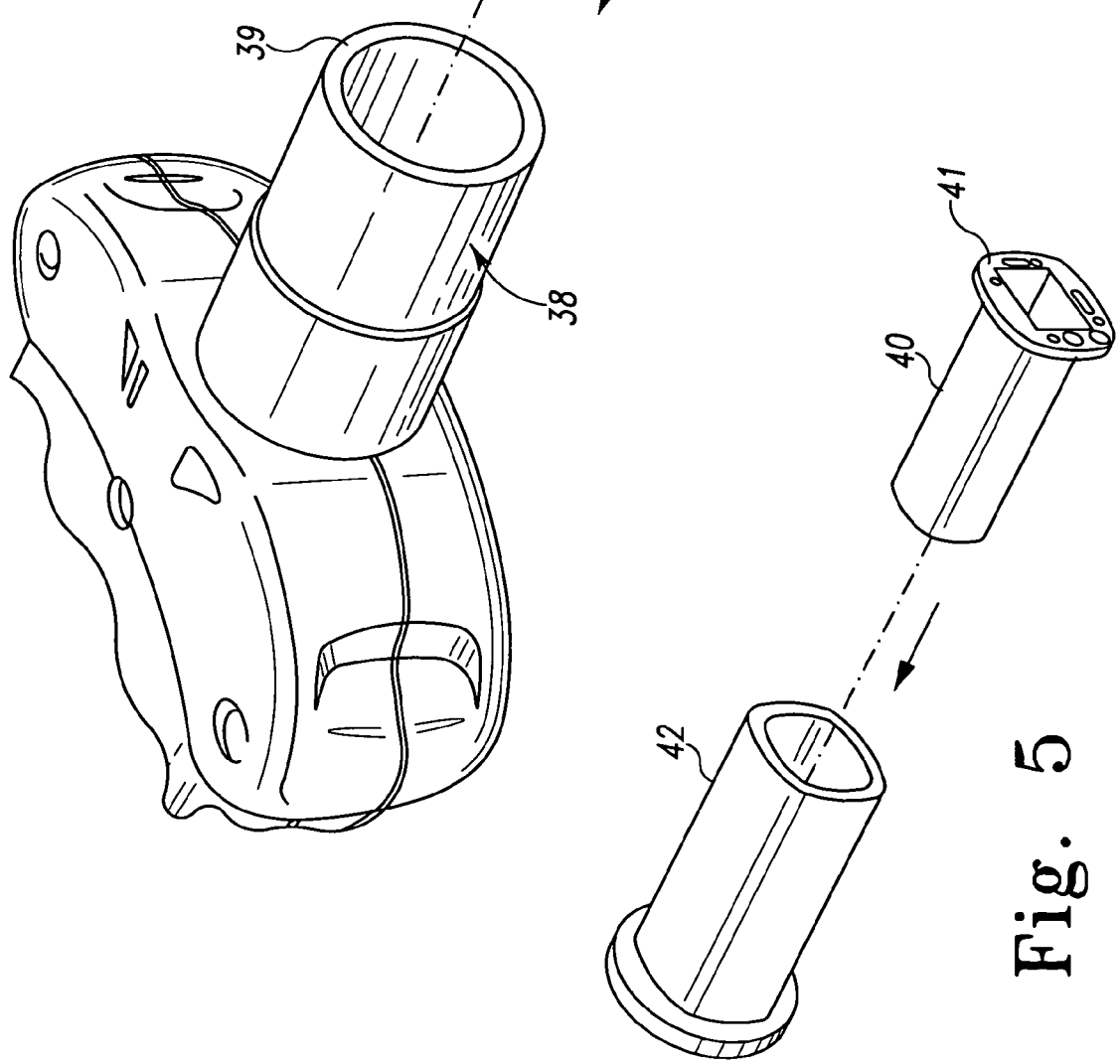
FIG. 5 is a perspective view of a collimator tube and an insert in one embodiment of the present invention.

As shown in FIG. 5, insert 40 is a step-down insert that can be inserted into collimator tube 42 to make the image capture area smaller. Alternatively or additionally, insert 40 can be used to add integrated devices to existing collimator tube 42. One non-limiting example of a situation in which insert 40 can be used is to capture an image more precisely on a smaller image receptor than collimator tube 42 would capture alone. Alternatively or additionally, insert 40 can be inserted into collimator tube adapter 34 of FIG. 4 to make the image capture area even smaller. Although not numbered on FIG. 5 to preserve clarity, instead of or in addition to the integrated devices included within the walls of collimator tube 14 or collimator tube adapter 34, insert 40 can optionally include one or more devices integrated within its walls. Insert 40 can optionally have at least one integrated device visible at least in part from end 41. Details about these integrated devices and how they function are described in detail in reference to FIGS. 1 and 4. Alternatively or additionally, insert 40 can be used to add one or more integrated devices to existing collimator tube 42 without reducing the size of the image capture area any more than necessary to house the integrated devices.

Figure 6:
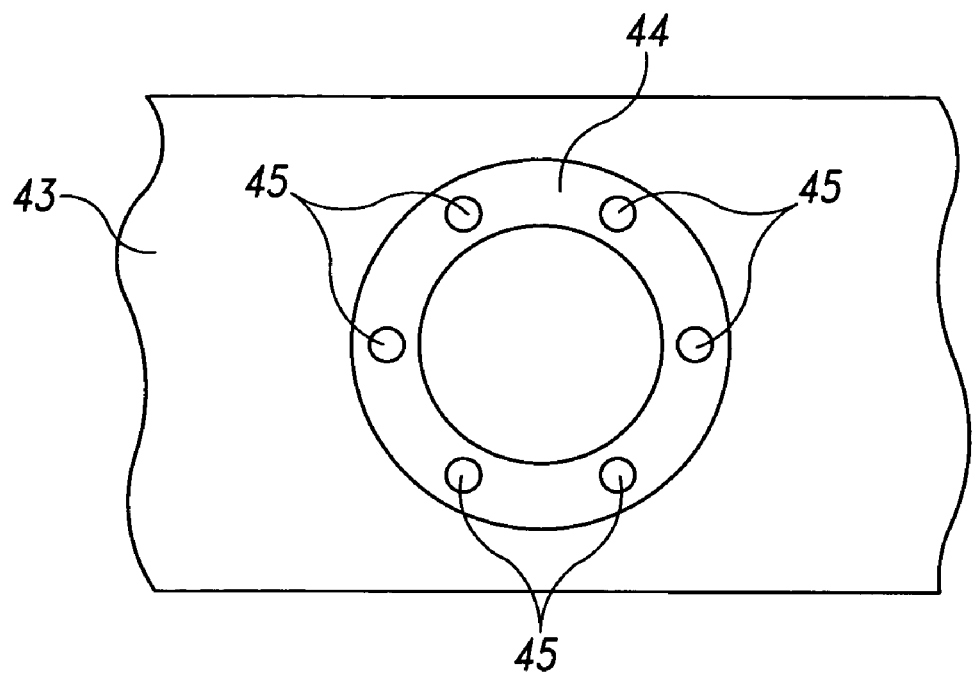
FIG. 6 is a front end view of an x-ray device without a collimator tube attached for one embodiment of the present invention.
Figure 7:
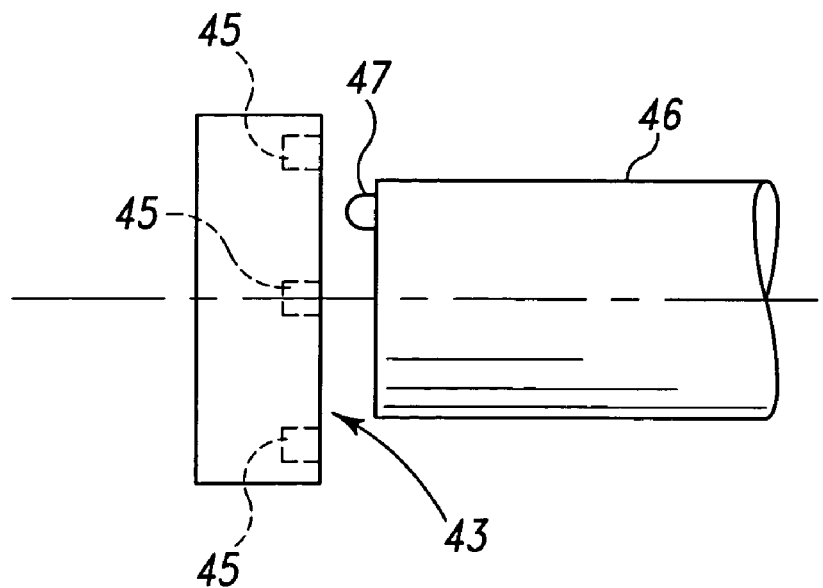
FIG. 7 is a partial elevational view of a collimator tube mating with the x-ray device of FIG. 6 in a manner that allows rotation of the collimator tube.

As shown in FIG. 6–7, in one embodiment, a collimator tube and/or x-ray generator can rotate with respect to the other. Front end of x-ray generator 43 can optionally include a circular or other path 44 with indentations 45. Collimator tube 46 mates with front end of x-ray generator 43 with one or more detents 47 that lock and unlock into one or more of indentations 45 when rotated along path 44. Circular or other path 44 can be a track or other types as would occur to one of ordinary skill in the art so as to allow collimator tube 46 inserted therein to remain physically attached to the front end of x-ray generator 43 and then click into position when coming into contact with one or more detents 47. In an alternative embodiment, the indentations and path are present on collimator tube 46 and one or more detents are present on front end of x-ray generator 43.

Figure 2:
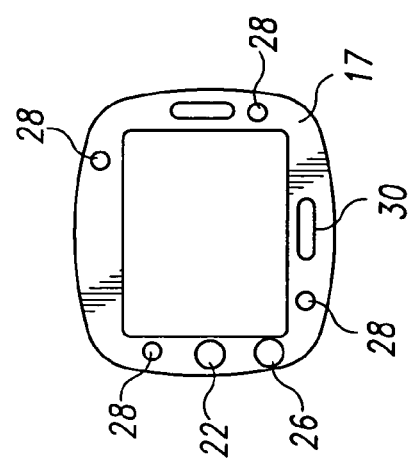
FIG. 2 is a front end view of a collimator tube of one embodiment of the current invention.
Figure 9:
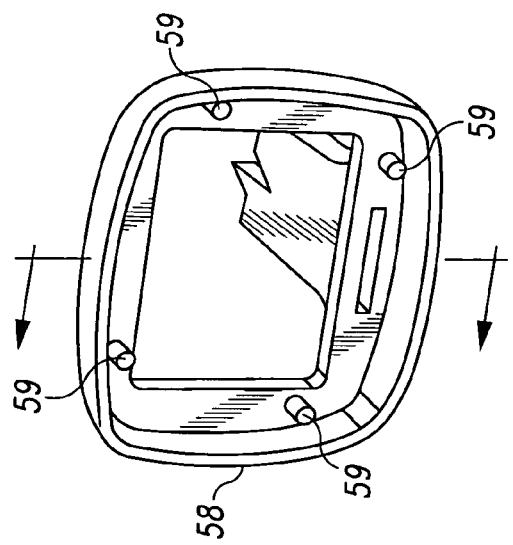
FIG. 9 is a back end view of a connection end of the receptor holder of FIG. 10.
Figure 10:
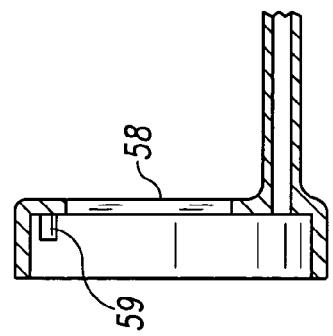
FIG. 10 is a partial cross-section view of the connection end of the receptor holder of FIG. 10.
Figure 8:
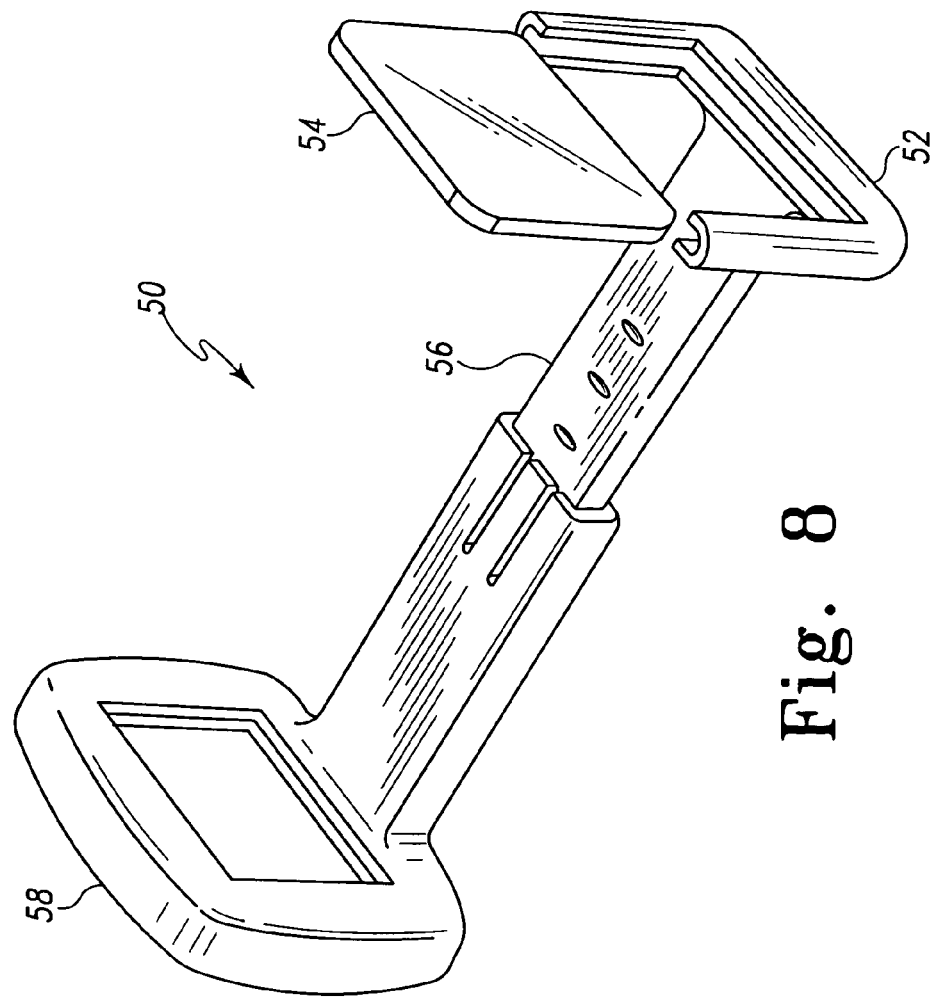
FIG. 8 is a side perspective view of a first embodiment receptor holder of the current invention.

Referring now to FIGS. 8–10 with continued reference to FIGS. 1–2, a first embodiment receptor holder 50 is illustrated. Receptor holder 50 has a holder end 52 that is operative to hold an image receptor 54, such as x-ray film or a digital charge-coupled device (CCD) sensor, as a few non-limiting examples. Receptor holder 50 has an adjustable bar 56 for adjusting the distance of holder end 52 from a connection end 58. In one embodiment, connection end 58 has a square shape. Connection end 58 can also be rectangular, star, cross or round in cross section shape, as a few additional non-limiting examples.

As shown in FIGS. 9 and 10, connection end 58 may have contact sensors 59 that are operative to be connected with collimator tube 14 through contact end receptors 28 formed in collimator tube end 17. In one embodiment, contact sensors 59 are used to ensure that the receptor holder 50 is attached to collimator tube 14 before firing the x-ray generator 12. In this embodiment, contact end receptors 28 are formed with sensors that determine when contact sensors 59 are inserted therein. As one example, each receptor 28 may have two metallic elements that are short circuited by a conductive contact sensor 59 when the connection end 58 is fitted to the collimator tube end 17. Coupling these metallic elements to the firing circuitry of the image capture device 10 can prevent the image capture device 10 from being fired unless the receptor holder 50 is properly fitted, as will be apparent to those skilled in the art from the above description. In one embodiment, receptor holder 50 is used to capture film-based x-ray images. In another embodiment, receptor holder is used to capture digitized x-ray images. Alternatively or additionally, receptor holder 50 can be used to hold a mirror for reflecting an image to be captured with camera 22, or for reflecting transilluminator light 26 for capture with camera 22.

Figure 11:
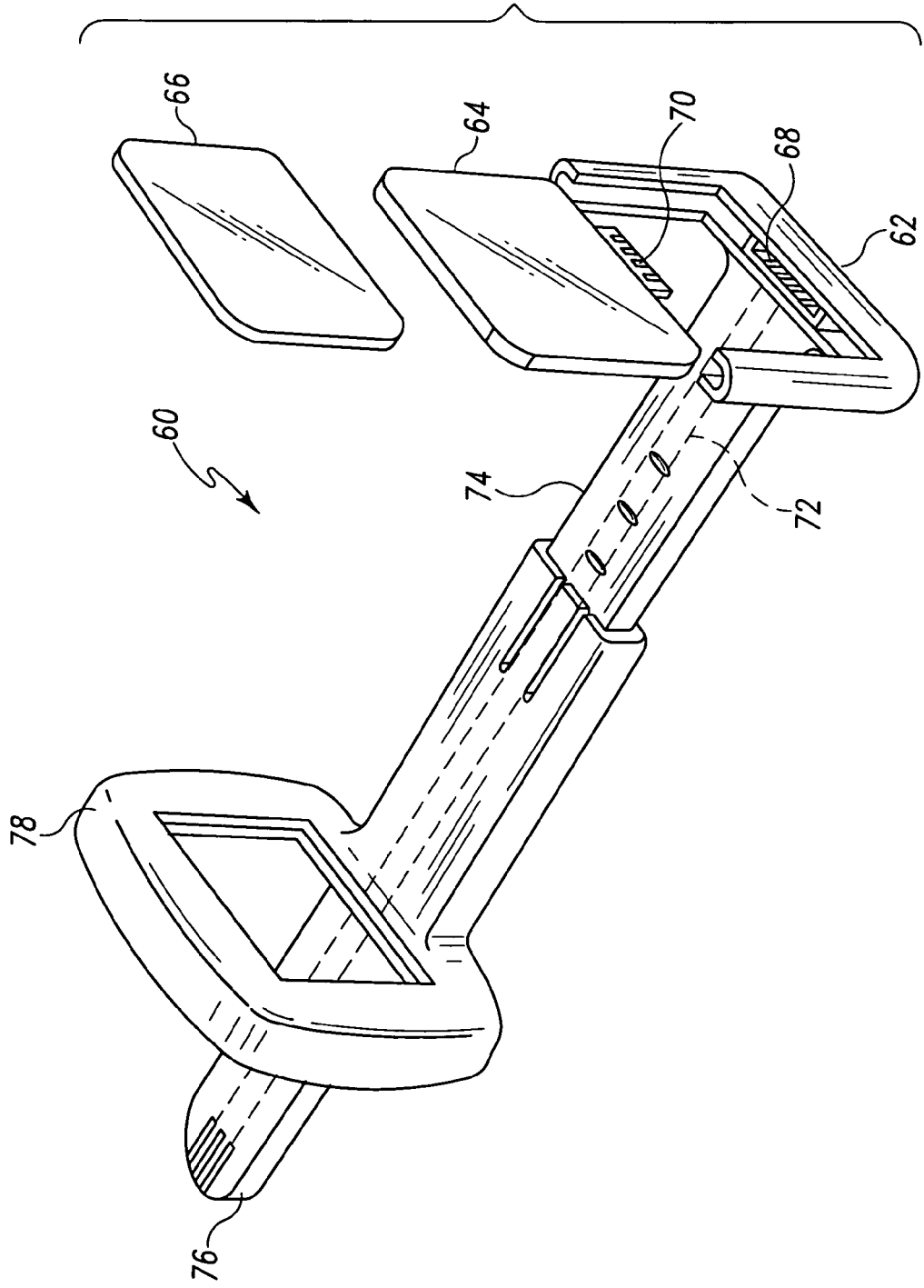
FIG. 11 is a side perspective view of a second embodiment receptor holder of the current invention.

Referring now to FIG. 11 with continued reference to FIGS. 1–2, a second embodiment receptor holder 60 is illustrated. Receptor holder 60 has a holder end 62 that is operative to hold a digital sensor 64 or x-ray film 66. Alternatively or additionally, receptor holder 60 can be used to hold a mirror for use with camera 22 or transilluminator light 26, as described hereinabove. Holder end 62 contains a docking port 68 to enable connection of digital sensor 64, which includes a sensor end 70 for electrical mating to docking port 68 of holder end 62. In one embodiment, wiring 72 is connected to docking port 68 at holder end 62. Wiring 72 runs through adjustable bar 74 and connects to contact end 76. Receptor holder 60 has adjustable bar 74 for adjusting the distance of holder end 62 from contact end 76. Contact end 76 can be inserted into contact end receptacle 30 of collimator tube 14 to couple receptor holder 60 to collimator tube 14.

Upon insertion of contact end 76 into contact end receptacle 30, connection frame 78 fits over end 17 of collimator tube 14. In one embodiment, when digital sensor 64 is docked in docking port 68 and x-ray generator 12 is fired, digital data is captured using sensor 64 and travels through wiring 72 to contact end 76 and to frame grabber 24 of collimator tube 14. In another embodiment, digital data captured using sensor 64 travels through wiring 72 to contact end 76 and to radio frequency transmitter 20 of collimator tube 14. In this embodiment, a frame grabber may be present in the remote computer.

In an alternate embodiment, receptor holder 50 (FIG. 8) and/or receptor holder 60 (FIG. 11) has an integrated radio frequency transmitter, such as within the walls of the holder.

Figure 12:
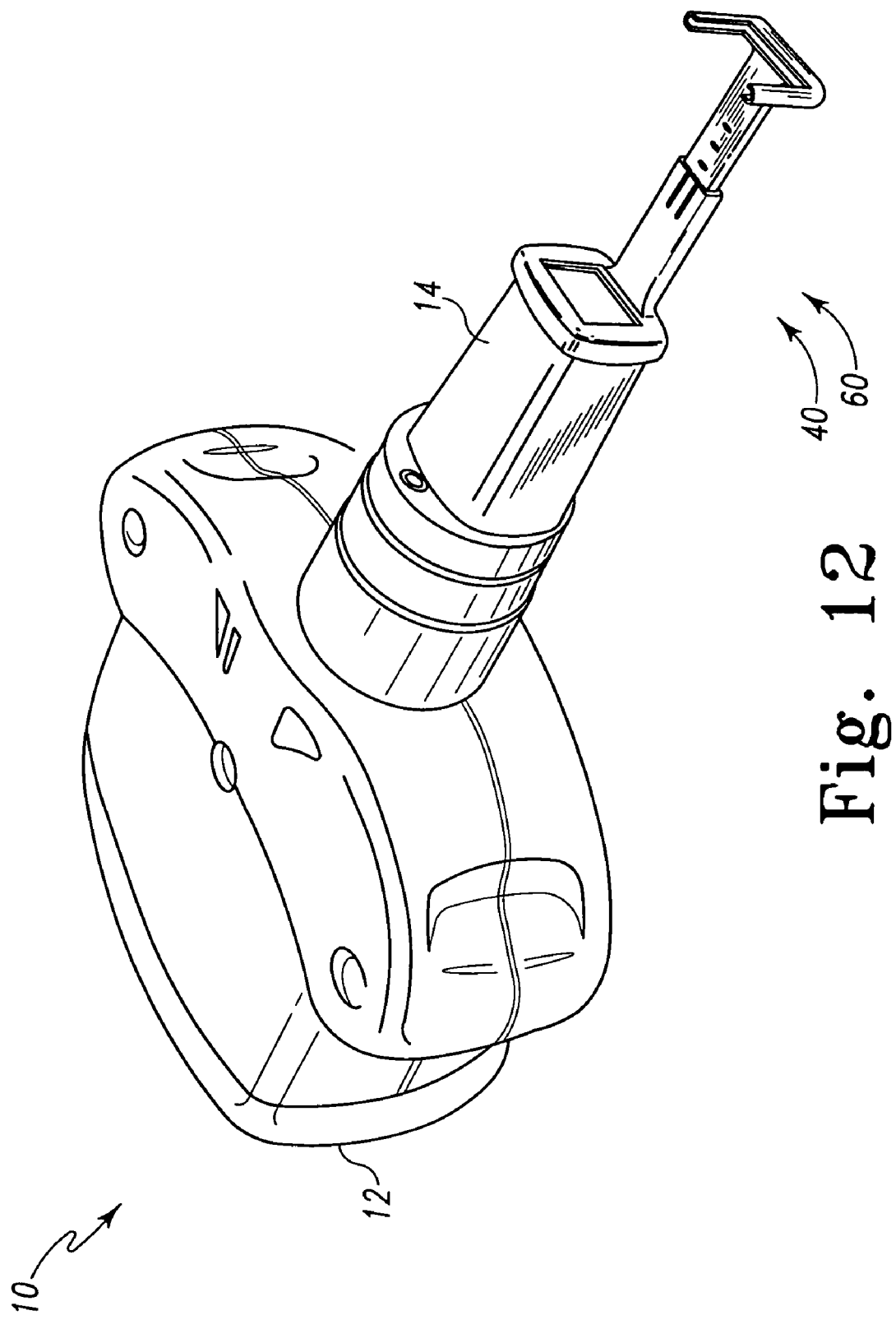
FIG. 12 is a perspective view of an image capture device illustrating an x-ray generator, collimator tube, and receptor holder of one embodiment of the present invention.

FIG. 12 illustrates an embodiment of the system of the present invention, comprising image capture device 10 with x-ray generator 12, collimator tube 14, and receptor holder (50 or 60) attached.

Figure 13:
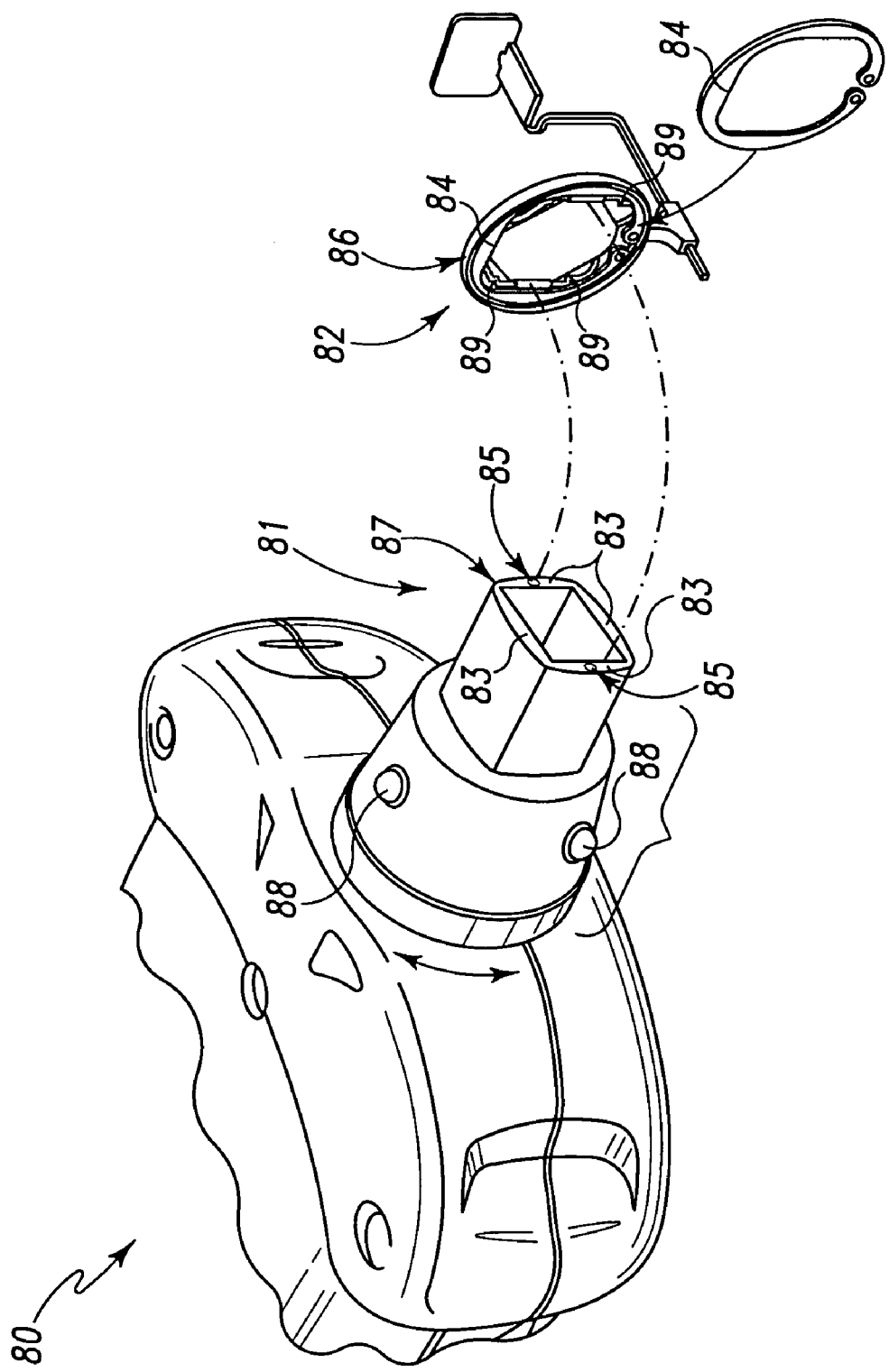
FIG. 13 is a side perspective view of an image capture device illustrating an x-ray generator, collimator tube, and receptor holder of one embodiment of the present invention.

FIG. 13 illustrates an image capture device having an x-ray generator 80, collimator tube 81, and receptor holder 82 of another embodiment of the present invention. Film alignment ring 86 of receptor holder 82 fits around outer perimeter 87 of collimator tube 81. In one embodiment, notches 89 in receptor holder 82 are tapered and/or indented to help film alignment ring 86 align properly with collimator tube 81. Receptor holder 82 can be coupled to collimator tube 81 by magnetism when magnets 83 of collimator tube 81 come into contact with conductor/magnet interface metal snap ring 84 of receptor holder 82. Alternatively or additionally, snap ring 84 completes the circuit between low voltage electrical contact 85 and magnets 83, causing LED lights 88 to illuminate to indicate that receptor holder 82 is properly coupled to collimator tube 81. Magnets 83 and/or electrical contacts 85 can be located at one or more of various locations on outer perimeter 87 or other locations as would occur to one of ordinary skill in the art. In one embodiment, collimator tube 81 is a replacement for a prior collimator tube of a differing shape, such as a rectangular tube replacing a round tube, to name a non-limiting example. Alternatively or additionally, magnets 83, electrical contacts 85, and LED lights 88 can be included in an adaptor that is attached to an existing collimator tube. In one embodiment, receptor holder 82 and collimator tube 81 maintain a magnetic connection sufficient to couple them together but to also to allow them to easily separate from each other upon contact, such as with a doctor or patient touching receptor holder 82. Alternatively or additionally, the positioning bar of receptor holder 82 has notches that allow the user to identify the distance at which the film was positioned, such as to allow for re-taking another image in the future at the same distance.

Although not shown on FIG. 13 to preserve clarity, in one embodiment, collimator tube 81 has one or more devices integrated within its walls. Collimator tube 81 can include the same devices and perform the same functions as described herein with respect to collimator tube 14 of image capture device 10 on FIG. 1.

Figure 14:
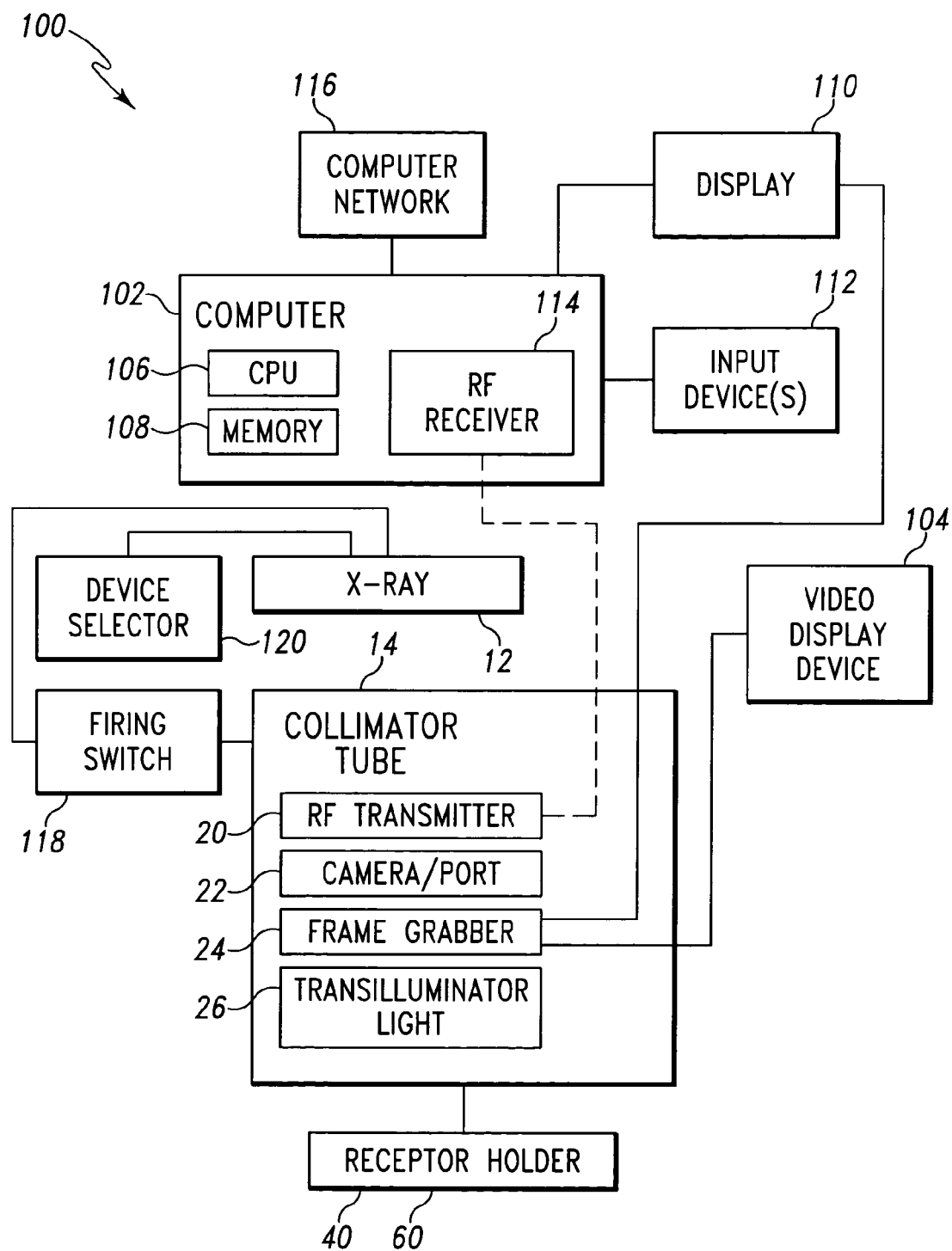
FIG. 14 is a diagrammatic view of a system of one embodiment of the present invention for use with the image capture device of FIGS. 1–13.
Figure 15:
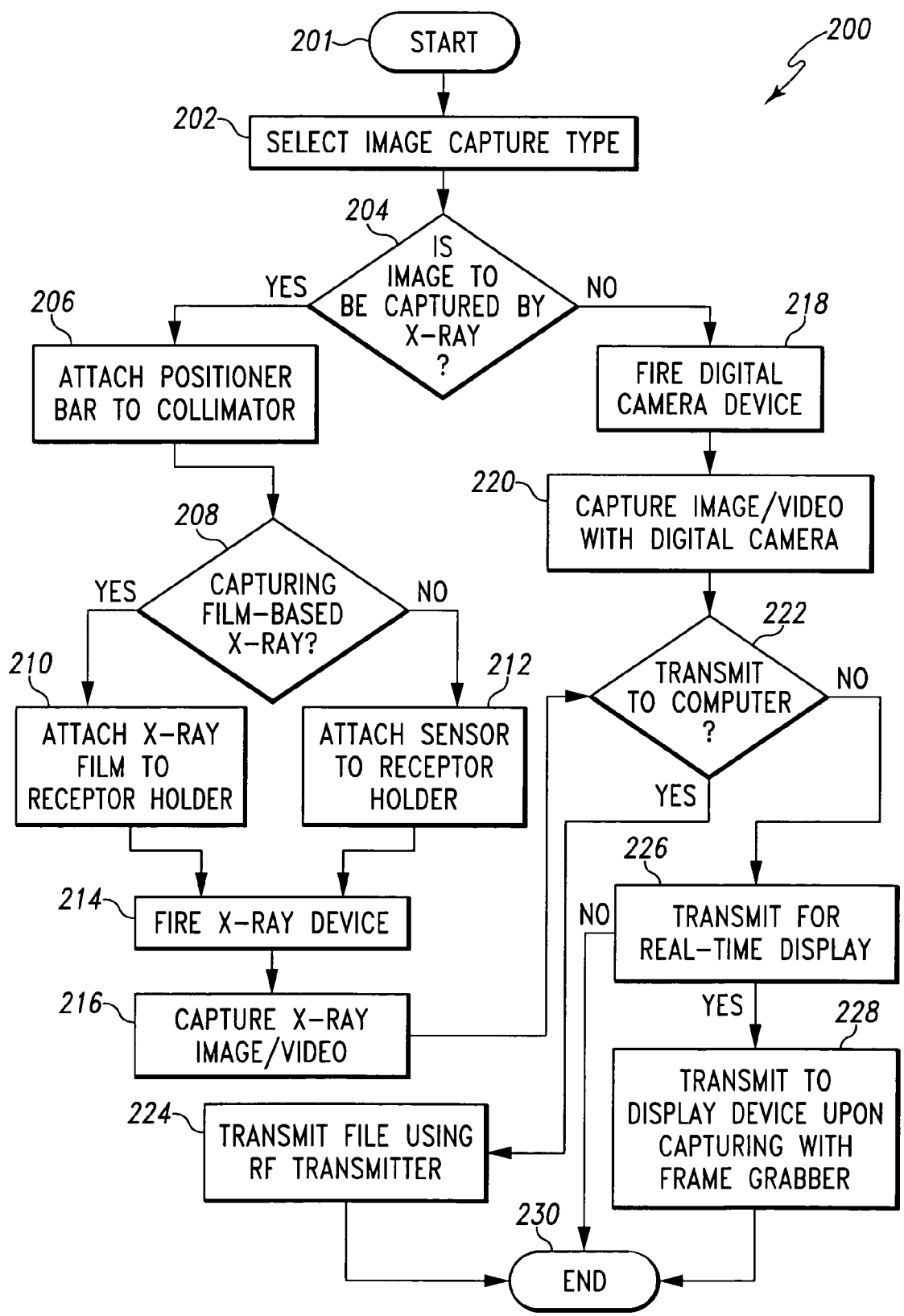
FIG. 15 illustrates a high-level process flow diagram for the system of FIG. 1 and the image capture device of FIGS. 1–13.

Reference will now be made to FIGS. 14 and 15 with continued reference to FIGS. 1–13 to illustrate a system and method for using image capture device 10. The same reference numerals are used to refer to elements that have already been introduced. FIG. 14 is a diagrammatic view of system 100 of one embodiment of the present invention. System 100 includes computer 102, x-ray generator 12, collimator tube 14, receptor holder (50 or 60), and video display device 104. It should be understood computer 102 may be arranged to include both a client and server, just a client, or just a server. Furthermore, it should be understood that while one computer is illustrated, more than one computer may be utilized in alternative embodiments.

Computer 102 includes one or more processors or CPUs 106 and one or more types of memory 108. Each memory 108 may include a removable memory device, although not shown to preserve clarity. The processor 106 may be comprised of one or more components configured as a single unit. Alternatively, when of a multi-component form, a processor 106 may have one or more components located remotely relative to the others. One or more components of each processor 106 may be of the electronic variety defining digital circuitry, analog circuitry, or both. In one embodiment, processor 106 is of a conventional, integrated circuit microprocessor arrangement, such as one or more PENTIUM III or PENTIUM 4 processors supplied by INTEL Corporation of 2200 Mission College Boulevard, Santa Clara, Calif. 95052, USA.

Memory 108 (removable or generic) is one form of computer-readable device. Memory 108 may include one or more types of solid-state electronic memory, magnetic memory, or optical memory, just to name a few. By way of non-limiting example, memory 108 may include solid-state electronic Random Access Memory (RAM), Sequentially Accessible Memory (SAM) (such as the First-In, First-Out (FIFO) variety or the Last-In-First-Out (LIFO) variety), Programmable Read Only Memory (PROM), Electronically Programmable Read Only Memory (EPROM), or Electrically Erasable Programmable Read Only Memory (EEPROM); an optical disc memory (such as a DVD or CD ROM); a magnetically encoded hard disc, floppy disc, tape, or cartridge media; or a combination of any of these memory types. Also, memory 108 may be volatile, nonvolatile, or a hybrid combination of volatile and nonvolatile varieties.

Computer 102 includes a display 110 and one or more input devices 112. Input devices 112 may include one or more operator input devices such as a keyboard, electronic pen input device, mouse, track ball, light pen, to name just a few representative examples. Computer includes a radio frequency (RF) receiver 114 for receiving data transmitted by radio frequency transmitters. Alternatively or additionally, computer 102 includes a printer. In one embodiment, computer 102 is disconnected from computer network 116. In another embodiment, computer 102 is connected to network 116.

Although only one computer 102 is shown to preserve clarity, more computers could also be present. In such instances, multiple computers 102, displays 110, and input devices 112 may be of the same respective type, or a heterogeneous combination of different computing devices. When more computers are present, computer 102 can be coupled to other computers over computer network 116. Computer network 116 could be in the form of a Local Area Network (LAN), Municipal Area Network (MAN), Wide Area Network (WAN), such as the Internet, a combination of these, or such other network arrangement as would occur to those skilled in the art. The one or more features provided by computer 102 can be provided on the same computer or varying other arrangements of computers at one or more physical locations and still be within the spirit of the invention.

X-ray generator 12 is operable to generate x-ray images. Collimator tube 14 serves as the means for focusing x-rays for x-ray device 12, and also includes additional integrated devices. Alternatively or additionally, collimator tube 14 also decreases scatter radiation and/or decreases absorbed radiation, thereby lowering the patient's x-ray dose. In one embodiment, collimator tube 14 has a radio frequency (RF) transmitter 20 that can communicate with RF receiver 114 of computer 102. Alternatively or additionally, collimator tube has an integrated camera 22. In one embodiment, camera 22 is a camera port for allowing an external camera device to plug into collimator tube 14. One non-limiting example of an external camera device includes an intra-oral camera 32 of FIG. 3. In another embodiment, camera 22 is wholly contained within collimator tube 14.

Alternatively or additionally, collimator tube 14 includes frame grabber 24 for capturing of and transmission of still and/or video images to video display device 104 and/or to display 110 of computer 102. Frame grabber 24 may also transfer data to rf transmitter 20. In one embodiment, collimator tube 14 includes transilluminator light 26. Transilluminator light 26 allows for shining a light through a tooth, body or organ, to name a few non-limiting examples.

X-ray generator 12 and collimator tube 14 are coupled to firing switch 118 and device selector 120. In one embodiment, a single firing switch 118 is used to fire whatever device is selected by device selector 120. In another embodiment, each image capture device has its own firing switch 118, and thus device selector 120 is not used. In some embodiments, firing switch 118 comprises a pair of switches which must both be pressed to activate the chosen device.

The operating logic of system 100 can be embodied in signals in programming instructions, dedicated hardware, transmitted over computer network 116, or a combination of these.

As one non-limiting example, system 100 can be used by a dentist to capture patient images. The image capture apparatus, system and method of the current invention are not limited to use in dentistry, or the field of medicine, as will be understood by one in the art. The current invention can be used in various industries where capturing an x-ray image or digital image would be useful.

Referring additionally to FIG. 15, one embodiment for implementation with system 100 is illustrated in flow chart form as procedure 200, which demonstrates a high level process flow diagram of some of the features provided by system 100. In one form, procedure 200 is at least partially implemented in the operating logic of system 100. Procedure 200 begins at start point 201 with selecting an image capture type (stage 202). In one embodiment, image capture type is selected using device selector 120.

If the image to be captured by image capture device 10 is an x-ray image (decision point 204), then a receptor holder (50 or 60) is attached to collimator tube 14 (stage 206). If the image is to be captured on x-ray film (decision point 208), then x-ray film is attached to receptor holder (50 or 60) (stage 210). If the image is to be captured using digital x-ray (decision point 208), then digital sensor 64 is attached to receptor holder 60 (stage 212). The x-ray generator 12 is then fired using firing switch 118 (stage 214) and the x-ray image(s) and/or video are captured (stage 216) by the film or the sensor 64.

If the image to be captured by image capture device 10 is not an x-ray image but instead is to be captured by digital camera (decision point 204), then digital camera 22 is fired using firing switch 118 (stage 218) and the digital image(s) and/or video are captured (stage 220).

If image(s) and/or video captured digitally with the x-ray generator 12 or the digital camera 22 are to be transmitted to a remote computer (decision point 222), then RF transmitter 20 sends the digital file(s) to RF receiver 114 of computer 102 (stage 224). If the image(s) and/or video captured digitally with the x-ray receptor 64 or the digital camera 22 are to be displayed in real-time (decision point 226), then frame grabber board 24 intercepts the images captured with sensor 64 or digital camera 22 accordingly and transmits them (using RF transmitter 20) to computer 102, video display device 104, or computer display 110 (stage 228). The process then ends at stage 230.

In another embodiment of the present invention, an apparatus for use with an x-ray generator is disclosed that comprises a collimator tube coupled to the x-ray generator; a camera integrated with the collimator tube, said camera being operable to capture digital images; and a radio frequency transmitter integrated with the collimator tube and operably coupled to the camera, said radio frequency transmitter being operable to transmit digital images captured by the camera to a remote receiver.

In yet another embodiment of the present invention, an apparatus for use with an x-ray generator is disclosed that comprises a collimator tube coupled to the x-ray generator; a digital sensor operable to capture x-ray images; and a frame grabber integrated with the collimator tube, said frame grabber operatively coupled to the sensor and operable to capture images for display on an external display device.

In yet a further embodiment of the present invention, a method is disclosed that comprises providing an image capture device having a plurality of devices to use for capturing an image, wherein one of the plurality of devices for capturing an image is an x-ray generator and one of the plurality of devices for capturing an image is an image capturing device integrated within a collimator tube; from the image capture device, receiving a selection for an image capture type that specifies at least one of a plurality of devices to use for capturing an image; receiving a fire command to fire the image capture device; and capturing at least one image with the image capture device.

In another embodiment of the present invention, a system is disclosed that comprises: an external device, said external device having at least a display; an x-ray generator; a collimator tube coupled to the x-ray generator, said collimator tube having at least one integrated digital image capture device; means for receiving a fire command and capturing at least one image with the at least one integrated digital image capture device; and means for transmitting the captured image to the external device upon receiving the fire command.

In another embodiment, an apparatus for use with an x-ray generator is disclosed that comprises a collimator tube coupled to the x-ray generator, said collimator tube having one or more walls; and at least one device contained within said one or more walls of the collimator tube.

In yet a further embodiment, an apparatus for use with an x-ray generator is disclosed that comprises: a collimator tube coupled to the x-ray generator; and a plurality of magnets coupled to collimator tube, said magnets being operable to couple the collimator tube to a receptor holder through magnetism.

All publications, prior applications, and other documents cited herein are hereby incorporated by reference in their entirety as if each had been individually incorporated by reference and fully set forth.

A person of ordinary skill in the computer software art will recognize that the client and/or server arrangements could be organized differently to include fewer or additional options or features than as portrayed in the illustrations and still be within the spirit of the invention.

While the invention has been illustrated and described in detail in the drawings and foregoing description, the same is to be considered as illustrative and not restrictive in character, it being understood that only the preferred embodiment has been shown and described and that all equivalents, changes, and modifications that come within the spirit of the inventions as described herein and/or by the following claims are desired to be protected.

What is claimed is:

1. An apparatus for use with an X-ray generator, the apparatus comprising:
   a collimator tube coupled to the X-ray generator;
   a camera coupled to the collimator tube, said camera being operable to capture digital images in a visible portion of the electromagnetic spectrum; and
   a radio frequency transmitter operably coupled to the camera, said radio frequency transmitter being operable to transmit digital images captured by the camera to a remote receivers;
   wherein the collimator tube comprises one or more walls and the camera and the radio frequency transmitter are contained within said one or more walls of the collimator tube.

2. The apparatus of claim 1, wherein the camera is an intra-oral camera coupled to the collimator tube via a camera port.

3. The apparatus of claim 1, further comprising:
   a frame grabber operably coupled to the camera, said frame grabber being operable to capture images from the camera for display on an external display device.

4. The apparatus of claim 3, wherein the collimator tube comprises one or more walls and the frame grabber is contained within said one or more walls of the collimator tube.

5. The apparatus of claim 1, further comprising:
   a transilluminator light coupled to the collimator tube.

6. The apparatus of claim 5, wherein the collimator tube comprises one or more walls and the transilluminator light is contained within said one or more walls of the collimator tube.

7. The apparatus of claim 1, further comprising:
   a receptor holder coupled to the collimator tube, said receptor holder being operable to hold an X-ray film for capturing an X-ray image.

8. The apparatus of claim 1, further comprising:
a receptor holder coupled to the collimator tube, said receptor holder being operable to hold a digital X-ray sensor and to couple the sensor to the collimator tube.

9. An apparatus for use with an X-ray generator, the apparatus comprising:
a collimator tube coupled to the X-ray generator;
a digital sensor operable to capture X-ray images; and
a frame grabber integrated with the collimator tube, said frame grabber operatively coupled to the sensor and operable to capture images for display on an external display device.

10. The apparatus of claim 9, further comprising:
a receptor holder coupled to the collimator tube, said receptor holder being operable to hold the sensor and to couple the sensor to the frame grabber through a connecting wire, whereby a digital X-ray image can be captured.

11. The apparatus of claim 9, wherein the collimator tube comprises one or more walls and the frame grabber is contained within said one or more walls of the collimator tube.

12. An apparatus for use with an X-ray generator, the apparatus comprising:
a collimator tube coupled to the X-ray generator, said collimator tube having one or more walls; and
at least one image capture device contained within said one or more walls of the collimator tube.

13. The apparatus of claim 12, wherein the at least one device includes a camera, said camera being operable to capture digital images.

14. The apparatus of claim 12, further comprising:
a digital sensor operable to capture X-ray images; and
a radio frequency transmitter coupled to said collimator tube, said radio frequency transmitter being operable to transmit digital images captured with the digital sensor to a remote receiver.

15. The apparatus of claim 12, wherein the at least one device includes a camera and a transilluminator light, said camera being operable to capture digital images, and said transilluminator light being operable to illuminate an area to be captured by the camera.

16. The apparatus of claim 12, wherein the collimator tube comprises:
an original collimator tube of a first shape;
a collimator tube adapter of a second shape coupled to the original collimator tube to form a modified collimator tube;
and wherein said at least one device is contained within one or more walls of the collimator tube adapter.

17. The apparatus of claim 16, wherein the collimator tube adapter has a cap for securing the collimator tube adapter to an end of the original collimator tube, and wherein the collimator tube adapter has a spacing means to allow a body portion of the collimator tube adapter to remain securely in place inside an inner periphery of the original collimator tube when the cap is secured over the end.

18. The apparatus of claim 12, wherein the X-ray generator was originally designed to work with a detachable collimator tube formed of a first shape, and wherein the collimator tube is formed of a second shape.

19. The apparatus of claim 12, wherein the collimator tube comprises:
an original collimator tube;
a step-down insert coupled to the original collimator tube to reduce a size of the original collimator tube; and
wherein said at least one device is contained within one or more walls of the collimator tube adapter.

20. The apparatus of claim 12, wherein the collimator tube is operable to rotate in position with respect to the X-ray generator.

21. An apparatus for use with an X-ray generator, the apparatus comprising:
a collimator tube coupled to the X-ray generator; and
a plurality of magnets operable to couple the collimator tube to a receptor holder through magnetism.

22. The apparatus of claim 21, wherein:
said plurality of magnets are coupled to said collimator tube; and
a metallic plate coupled to the receptor holder, said metallic plate being adapted to couple with said magnets.

23. A method comprising:
providing an apparatus having a plurality of image capturing devices and a collimator tube, wherein one of the image capturing devices is an X-ray generator and one of the image capturing devices is a camera coupled to the collimator tube, said camera being operable to capture images in a visible portion of the electromagnetic spectrum;
from the apparatus, receiving a selection of an image capture device to use for capturing an image;
if the selected image capture device is an intra-oral camera, performing the following steps prior to receiving the fire command:
attaching a receptor holder to the collimator tube;
attaching a mirror to the receptor holder;
illuminating a transilluminator light such that the emitted light shines through a tooth;
receiving a fire command to fire the image capture device;
capturing an image of the transilluminated tooth with the intra-oral camera.

24. An apparatus for use with an X-ray generator, the apparatus comprising:
a collimator tube having an end, said collimator tube being coupled to the X-ray generator;
a receptor holder adapted to be coupled on said end of said collimator tube, said receptor holder operable to hold an image receptor; and
an indicator which indicates when said receptor holder is coupled on the end of said collimator tube.

25. The apparatus of claim 24, wherein said indicator includes:
a contact sensor receptacle on said collimator tube;
a contact sensor on said receptor holder; and
wherein said contact sensor makes a connection with said contact sensor receptacle when said receptor holder is coupled on the end of said collimator tube.

26. The apparatus of claim 24, wherein said indicator is a light on said collimator tube which illuminates when said receptor holder is coupled on the end of said collimator tube.

27. The apparatus of claim 24, wherein said indicator emits an audible sound when said receptor holder is coupled on the end of said collimator tube.

28. The apparatus of claim 24, wherein said indicator prohibits the X-ray generator from firing unless said receptor holder is coupled on the end of said collimator tube.

29. A system comprising:
an X-ray generator;
a collimator tube coupled to said X-ray generator;
a receptor holder adapted to be coupled to said collimator tube;
an X-ray sensor operable to capture an X-ray image; and a sensor docking port on said receptor holder, said sensor docking port operable to make an electrical connection with said X-ray sensor when said X-ray sensor is docked on the docking port, said sensor docking port further operable to secure said X-ray sensor in position to receive a radiation dose emitted from said X-ray generator.

30. The system of claim 29, further comprising:
a display operable to receive data from said sensor docked on said sensor docking port, said display further operable to display said X-ray image captured by said X-ray sensor.

31. The system of claim 29, further comprising:
a radio frequency transmitter operable to receive data from said sensor docked on said sensor docking port, said radio frequency transmitter being further operable to transmit data from said X-ray sensor.

32. The system of claim 31, further comprising:
a display operable to receive data from said sensor docked on said sensor docking port, said display further operable to display said X-ray image captured by said X-ray sensor.

33. The system of claim 29, wherein said sensor docking port is electrically connected to said collimator tube when said receptor holder is coupled to said collimator tube.

34. The system of claim 29, further comprising:
a contact end on said receptor holder;
a contact end receptacle in said collimator tube adapted to be coupled to said contact end when said receptor holder is coupled to said collimator tube; and
wherein said contact end receptacle is operable to make an electrical connection to said sensor docking port through said contact end when said receptor holder is coupled to said collimator tube.

35. A system comprising:
an X-ray generator;
a collimator tube coupled to said X-ray generator;
a receptor holder adapted to be coupled to said collimator tube;
an X-ray sensor operable to capture an X-ray image;
a sensor docking port on said receptor holder, said sensor docking port operable to make an electrical connection with said X-ray sensor when said X-ray sensor is docked on the docking port, said sensor docking port further operable to secure said X-ray sensor in position to receive a radiation dose emitted from said X-ray generator; and
a radio frequency transmitter operable to receive data from said sensor, said radio frequency transmitter being further operable to transmit data from said X-ray sensor.

36. The system of claim 35 further comprising:
a display operable to display said X-ray image captured by said X-ray sensor.

37. An apparatus for use with an X-ray generator having a collimator tube, the apparatus comprising:
a collimator insert, said collimator insert being operable to be coupled to the collimator tube to reduce a size of the collimator; and
a device contained within a wall of said collimator insert;
wherein said collimator insert extends into an interior space of the collimator tube when said collimator insert is coupled to said collimator tube.

38. The apparatus of claim 37, wherein said collimator insert extends substantially the entire length of the collimator tube when said collimator insert is coupled to said collimator tube.

39. The apparatus of claim 37, wherein the collimator tube has a first shape in cross-section and said collimator insert has a second shape in cross-section different than said first shape.

40. The apparatus of claim 37, wherein the image capture area of said collimator insert is smaller than the image capture area of the collimator tube.

41. The apparatus of claim 37, further comprising:
a cap on said collimator insert operable to form a seal around an end of the collimator tube; and
a spacer on said collimator insert operable to secure said collimator insert inside the collimator tube.

42. The apparatus of claim 41, wherein said cap is operable to slide along said collimator insert to accommodate different lengths of the collimator tube.

43. The apparatus of claim 37, wherein said device is a digital camera.

44. The apparatus of claim 37, further comprising:
a digital sensor operable to capture X-ray images; and
wherein said device is a radio frequency transmitter operable to transmit digital images captured with the digital sensor to a remote receiver.

45. The apparatus of claim 37, wherein said collimator insert is operable to rotate in position with respect to the X-ray generator.

46. An apparatus for use with an X-ray generator having a collimator tube, the apparatus comprising:
a collimator insert, said collimator insert being operable to be coupled to the collimator tube to reduce a size of the collimator tubes; and
a receptor holder adapted to be coupled to said collimator inserts;
wherein said collimator insert extends into an interior space of the collimator tube when said collimator insert is coupled to said collimator tube.

47. The apparatus of claim 46, wherein said collimator insert extends substantially the entire length of the collimator tube when said collimator insert is coupled to said collimator tube.

48. The apparatus of claim 46, wherein the collimator tube has a first shape in cross-section and said collimator insert has a second shape in cross-section different than said first shape.

49. The apparatus of claim 46, wherein the image capture area of said collimator insert is smaller than the image capture area of the collimator tube.

50. The apparatus of claim 46, further comprising:
a cap on said collimator insert operable to form a seal around an end of the collimator tube; and
a spacer on said collimator insert operable to secure said collimator insert inside the collimator tube.

51. The apparatus of claim 50, wherein said cap is operable to slide along said collimator insert to accommodate different lengths of the collimator tube.

52. The apparatus of claim 46, wherein said device is a digital camera.

53. The apparatus of claim 46, further comprising:
a digital sensor operable to capture X-ray images; and
wherein said device is a radio frequency transmitter operable to transmit digital images captured with the digital sensor to a remote receiver.

54. The apparatus of claim 46, wherein said collimator insert is operable to rotate in position with respect to the X-ray generator.

55. An apparatus for use with an X-ray generator, the apparatus comprising:
a collimator tube coupled to the X-ray generator;

an intra-oral camera coupled to the collimator tube via a camera port, said intra-oral camera being operable to capture digital images in a visible portion of the electromagnetic spectrum; and
a radio frequency transmitter operably coupled to the camera, said radio frequency transmitter being operable to transmit digital images captured by the camera to a remote receiver.

56. The apparatus of claim 55, further comprising:
a transilluminator light coupled to the collimator tube.

57. The apparatus of claim 56, wherein the collimator tube comprises one or more walls and the transilluminator light is contained within said one or more walls of the collimator tube.

* * * * *

UNITED STATES PATENT AND TRADEMARK OFFICE
CERTIFICATE OF CORRECTION

| | |
|---|---|
| PATENT NO. | : 7,194,064 B2 |
| APPLICATION NO. | : 11/063959 |
| DATED | : March 20, 2007 |
| INVENTOR(S) | : Michael R. Razzano, Ronald C. Webb and Barry R. Margraf |

It is certified that error appears in the above-identified patent and that said Letters Patent is hereby corrected as shown below:

In column 10, line 42, please change "receivers" to --receiver--
In column 13, line 59, please add the word --tube-- after the word "collimator"
In column 14, line 30, please change "tubes" to --tube--
In column 14, line 32, please change "inserts" to --insert--

Signed and Sealed this

Tenth Day of July, 2007

JON W. DUDAS
*Director of the United States Patent and Trademark Office*